United States Patent [19]

Smith et al.

[11] Patent Number: 4,801,589

[45] Date of Patent: Jan. 31, 1989

[54] METHOD FOR SUPPRESSING THE IMMUNE RESPONSE

[75] Inventors: Sidney R. Smith, Ridgewood; Marvin I. Siegel, Woodbridge, both of N.J.

[73] Assignee: Schering Corporation, Kenilworth, N.J.

[21] Appl. No.: 871,691

[22] Filed: Jun. 12, 1986

[51] Int. Cl.$^4$ ............................................. A61K 31/44
[52] U.S. Cl. .................................... 514/291; 514/293
[58] Field of Search ................................ 514/291, 293

[56] References Cited

U.S. PATENT DOCUMENTS 4,680,298  7/1987  Blythin .............................. 514/293

FOREIGN PATENT DOCUMENTS 0127135  12/1984  European Pat. Off. ............ 514/293

OTHER PUBLICATIONS

Bulletin de la Societe Chimique de France, No. 1, 1968, pp. 364–369, C. Fournier, et al.
Derwent Abstract of Japanese Published Patent No. 58-144391 (8/83).
Journal of The Chemical Society, Perkins Transactions 1, Sep. 1983, pp. 2077–2087, London, G.B., D. G. Hawkins, et al.
Chemical Abstracts, vol. 101, No. 5, Jul. 30, 1984, p. 504, No. 38382t, E. M. Peresleni, et al.

*Primary Examiner*—Jerome D. Goldberg
*Attorney, Agent, or Firm*—Joseph T. Majka; James R. Nelson; Stephen I. Miller

[57] ABSTRACT

A method and composition for suppressing the immune response are disclosed which employ an immunosuppressing effective amount of certain substituted quinoline, naphthyridine and pyrido-pyrazine derivatives.

28 Claims, No Drawings

METHOD FOR SUPPRESSING THE IMMUNE RESPONSE

BACKGROUND OF THE INVENTION

The present invention relates to the use of certain tricyclic quinoline, naphthyridine and pyridopyrazine derivatives in suppressing the immune response.

The preparation of the compound 2'-methylpyrano-5',6':3,4-(2-oxo-1,2-dihydroquinoline) and its N-phenyl derivative is described in Bull. Soc. Chim. Fr., pp. 364-9 (1968) (C.A. 68: 114419c).

European published Application No. 84105923.1 (European patent publication No. 0 127 135) discloses the use of tricyclic quinoline, naphthyridine and pyridopyrazine derivatives in treating allergies, inflammation and peptic ulcers.

SUMMARY OF THE INVENTION

The present invention is drawn to a method for suppressing the immune response in a mammal which comprises administering to a mammal in need of such treatment an immunosuppressing effective amount of a compound having the structural formula I:

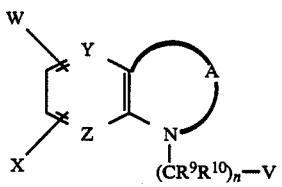

wherein:

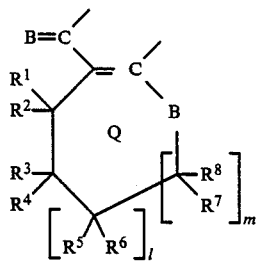

or

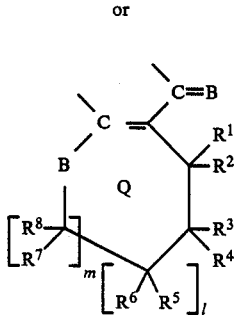

B is independently oxygen or sulfur;

$R^1$-$R^8$ may be the same or different and are hydrogen or alkyl having from 1 to 6 carbon atoms or two adjacent $R^1$-$R^8$ substituents may be combined to form an additional carbon to carbon bond;

l and m may be the same or different and are 0 or one;

the ring labeled, Q, may optionally contain up to two additional double bonds;

n is 0, 1 or 2;

W and X may be the same or different and are hydrogen, hydroxy, alkyl having from 1 to 6 carbon atoms, halogen, nitro, alkoxy having from 1 to 6 carbon atoms, trifluoromethyl, cyano, cycloalkyl having from 3 to 7 carbon atoms, alkenyloxy having from 3 to 6 carbon atoms, alkynyloxy having from 3 to 6 carbon atoms, $S(O)_p$—$R^a$ {wherein p is 0, 1 or 2 and $R^a$ is alkyl having from 1 to 6 carbon atoms}, $NHSO_2R^a$ {wherein $R^a$ is defined herein}, $NHSO_2CF_3$, $NHCOCF_3$, $SO_2NH_2$, $COR^b$ {wherein $R^b$ is OH, $NH_2$ or $OR^a$ (wherein $R^a$ is defined herein)}, O—D—$COR^b$ {wherein D is alkylene having from 1 to 4 carbon atoms and $R^b$ is defined herein}, $NHCOR^c$ {wherein $R^c$ is hydrogen, alkyl having from 1 to 6 carbon atoms, alkoxy having from 1 to 6 carbon atoms, $COR^d$ (wherein $R^d$ is hydroxy or alkoxy having from 1 to 6 carbon atoms) or $NHR^e$ (wherein $R^e$ is hydrogen or alkyl having from 1 to 6 carbon atoms)}, or phenoxy {wherein the benzene ring may be substituted with any of the other substituents W and X};

Y and Z may be the same or different and are CH or N;

V is phenyl, naphthyl, indenyl, indanyl, 2-, 3- or 4-pyridyl, 2-, 3- or 5-pyrimidinyl, 2- or 3-thienyl, 2- or 3-furyl or 2-, 4- or 5-thiazolyl, any of which may be substituted with W and X as defined herein; and $R^9$ and $R^{10}$ are independently hydrogen or alkyl having from 1 to 6 carbon atoms.

A subgenus of compounds is that wherein B is oxygen.

Another subgenus of compounds is that wherein B is oxygen and A is A'.

Still other subgenuses of compounds are those having the structural formulas:

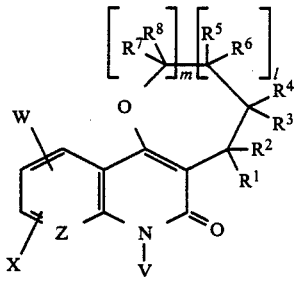

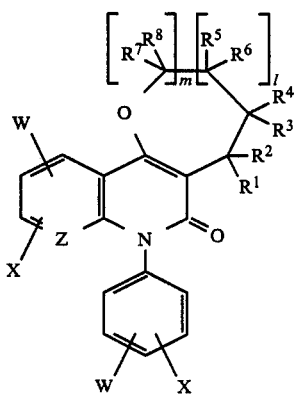

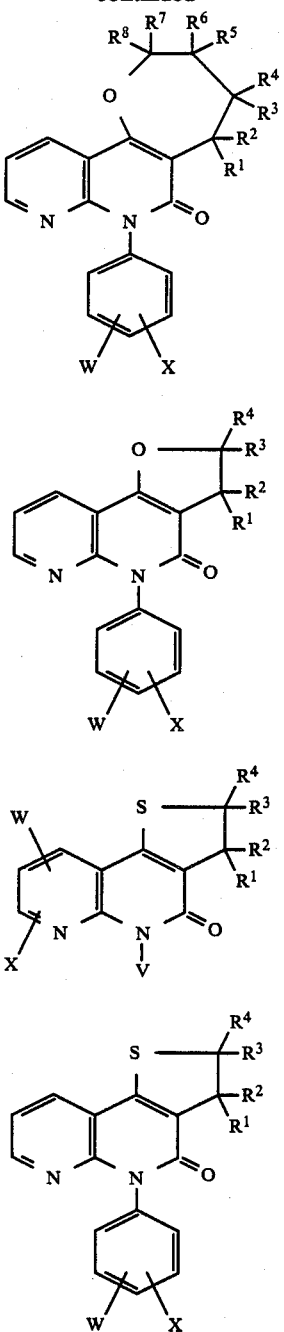

wherein V, W, X, Z, $R^1$–$R^8$, l and m are as defined herein.

Individual compounds suitable for use in the method and composition of the invention include those having the names: 3,5-dihydro-5-phenyl-furo[3,2-c][1,8]naphthyridin-4[2H]-one;
3,5-dihydro-5-phenyl-thieno[3,2-c][1,8]naphthyridin-4[2H]-one;
6-phenyl-2,3,4,6-tetrahydro-pyrano[3,2-c][1,8]naphthyridin-5-one;
2-methyl-3,5-dihydro-5-phenyl-furo[3,2-c][1,8]naphthyridin-4[2H]-one;
3,9-dihydro-9-phenyl-furo[2,3-b][1,8]naphthyridin-4[2H]-one;
3,9-dihydro-9-(p-methylphenyl)-furo[2,3-b][1,8]naphthyridin-4[2H]-one;
3,9-dihydro-2-methyl-9-phenyl-furo[2,3-b][1,8]naphthyridin-4[2H]-one;
3,5-dihydro-5-(p-methylphenyl)-furo[3,2-c][1,8]naphthyridin-4[2H]-one;
3,5-dihydro-5-(p-fluorophenyl)-furo[3,2-c][1,8]naphthyridin-4[2H]-one;
3,5-dihydro-5-(m-methoxyphenyl)-furo-[3,2-c][1,8]naphthyridin-4[2H]-one;
3,5-dihydro-5-(m-methylthiophenyl)-furo[3,2-c][1,8]naphthyridin-4[2H]-one;
3,9-dihydro-9-(p-fluorophenyl)-furo[2,3-b][1,8]naphthyridin-4[2H]-one;
3,9-dihydro-9-(m-methoxyphenyl)-furo[2,3-b][1,8]naphthyridin-4[2H]-one;
3,9-dihydro-9-(m-methylthiophenyl)-furo[3,2-c][1,8]naphthyridin-4[2H]-one;
3,5-dihydro-5-(3,4-dichlorophenyl)-furo[3,2-c][1,8]naphthyridin-4[2H]-one;
3,5-dihydro-5-(3,4-dichlorophenyl)-2-methyl-furo[3,2-c][1,8]-naphthyridin-4[2H]-one;
3,5-dihydro-5-(4-chlorophenyl)-furo[3,2-c][1,8]naphthyridin-4[2H]-one;
3,5-dihydro-5-(3-chlorophenyl)-furo[3,2-c][1,8]naphthyridin-4[2H]-one;
3,5-dihydro-5-(3-chlorophenyl)-2-methyl-furo[3,2-c][1,8]naphthyridin-4[2H]-one;
3,5-dihydro-5-(4-fluorophenyl)-2-methyl-furo[3,2-c][1,8]naphthyridin-4[2H]-one;
3,5-dihydro-5-(3-methoxyphenyl)-2-methyl-furo[3,2-c][1,8]-naphthyridin-4[2H]-one;
3,5-dihydro-5-(3,5-dichlorophenyl)-furo[3,2-c][1,8]naphthyridin-4[2H]-one;
3,5-dihydro-5-(3,5-dichlorophenyl)-2-methyl-furo[3,2-c][1,8]-naphthyridin-4[2H]-one;
3,5-dihydro-5-phenyl-2,2-dimethyl-furo[3,2-c][1,8]naphthyridin-4[2H]-one;
3,5-dihydro-5-(3-methylsulfonylaminophenyl)-2-methylfuro[3,2-c][1,8]-naphthyridin-4[2H]-one;
3,5-dihydro-5-(3-methylsulfonylaminophenyl)-furo[3,2-c][1,8]naphthyridin-4[2H]-one;
3,9-dihydro-9-(3,4-dichlorophenyl)-furo[2,3-b][1,8]naphthyridin-4[2H]-one;
3,9-dihydro-9-(4-chlorophenyl)-furo[2,3-b][1,8]naphthyridin-4[2H]-one;
3,9-dihydro-9-(3-chlorophenyl)-furo[2,3-b][1,8]naphthyridin-4[2H-one;
3,9-dihydro-9-(3-chlorophenyl)-2-methyl-furo[2,3-b][1,8]naphthyridin-4[2H]-one;
3,9-dihydro-9-(4-fluorophenyl)-2-methyl-furo[2,3-b][1,8]naphthyridin-4[2H]-one;
3,9-dihydro-9-(3-methoxyphenyl)-2-methyl-furo[2,3-b][1,8]-naphthyridin-4[2H]-one;
3,9-dihydro-9-(3,5-dichlorophenyl)-furo[2,3-b][1,8]naphthyridin-4[2H]-one;
3,9-dihydro-9-(3,5-dichlorophenyl)-2-methyl-furo[2,3-b][1,8]-naphthyridin-4[2H]-one;
3,9-dihydro-9-(3-methylsulfonylaminophenyl)-2-methyl-furo[2,3-b][1,8]-naphthyridin-4[2H]-one;
6-(4-chlorophenyl)-2,3,4,6-tetrahydro-5H-pyrano[3,2-c][1,8]naphthyridin-5-one;
6-(3,4-dichlorophenyl)-2,3,4,6-tetrahydro-5H-pyrano[3,2-c][1,8]naphthyridin-5-one;
6-(4-methoxyphenyl)-2,3,4,6-tetrahydro-5H-pyrano[3,2-c][1,8]naphthyridin-5-one;
6-(4-methylphenyl)-2,3,4,6-tetrahydro-5H-pyrano[3,2-c][1,8]naphthyridin-5-one;

10-(3,4-dichlorophenyl)-2,3,4,10-tetrahydro-5H-pyrano[2,3-b][1,8]naphthyridin-5-one;
10-(4-methoxyphenyl)-2,3,4,10-tetrahydro-5H-pyrano[2,3-b][1,8]naphthyridin-5-one;
10-(4-chlorophenyl)-2,3,4,10-tetrahydro-5H-pyrano(2,3-b][1,8]naphthyridin-5-one;
10-(4-methylphenyl)-2,3,4,10-tetrahydro-5H-pyrano(2,3-b][1,8]naphthyridin-5-one;
10-phenyl-2,3,4,10-tetrahydro-5H-pyrano-[2,3-b][1,8]-naphthyridin-5-one;
7-phenyl-3,4,5,7-tetrahydro-oxepino[3,2-c][1,8]-naphthyridin-6[2H]-one;
7-(4-chlorophenyl)-3,4,5,7-tetrahydro-oxepino[3,2-c][1,8]-naphthyridin-6[2H]-one;
7-(3-chlorophenyl)-3,4,5,7-tetrahydro-oxepino[3,2-c][1,8]-naphthyridin-6[2H]-one;
7-(3-methoxyphenyl)-3,4,5,7-tetrahydro-oxepino[3,2-c][1,8]-naphthyridin-6[2H]-one; and
7-(3-hydroxyphenyl)-3,4,5,7-tetrahydro-oxepino[3,2-c][1,8]-naphthyridin-6[2H]-one.

As disclosed in European published application No. 84105923.1 (European patent publication No. 0 127 135), these compounds possess anti-allergy and anti-inflammatory activities. It has now unexpectedly been found that these compounds possess immunosuppressive activity.

DESCRIPTION OF THE INVENTION

When utilized herein and in the appended claims the below listed terms, unless specified otherwise, are defined as follows:

halogen—fluorine, chlorine, bromine and iodine;
alkyl and alkoxy—comprised of straight and branched carbon chains containing from 1 to 6 carbon atoms;
alkenyloxy—comprised of straight and branched carbon chains containing from 3 to 8 carbon atoms and comprising a carbon to carbon double bond; and
alkynyloxy—comprised of straight and branched carbon chains containing from 3 to 8 carbon atoms and comprising a carbon to carbon triple bond.

The compounds of the invention may possibly contain two different "B" substituents. It is intended that both may simultaneously be oxygen or sulfur, or that either may be oxygen or sulfur.

In certain compounds of the invention, the ring labeled Q, may contain up to two additional double bonds which double bonds are formed by the combination of two adjacent substituents, $R^1$-$R^8$. Thus, for example, when Q is a 7 membered ring (l and m are both equal to 1) it may contain 3 double bonds. When multiple double bonds are present, they will be non-cumulated double bonds.

The compounds of the invention are comprised of a —$(CR^9R^{10})_n$— substituent wherein the $R^9$ and $R^{10}$ groups may vary independently. Thus, for example, when n equals 2, the following patterns of substitution (wherein hydrogen and $CH_3$ are used to represent any substituent, $R^9$ or $R^{10}$,) are contemplated: —C(CH$_3$)$_2$CH$_2$—, —CH$_2$C(CH$_3$)$_2$—, —CH$_2$CH(CH$_3$)—, —CH(CH$_3$)CH$_2$—, —(C(CH$_3$)H)$_2$— and the like. In addition when n equals 2, substituents such as —C(CH$_3$)$_2$CH(C$_2$H$_5$)—, —CH(CH$_3$)CH(C$_2$H$_5$)—, —CH(i—C$_3$H$_7$)CH(C$_2$H$_5$)— are also contemplated.

Certain compounds of the invention may exist in isomeric forms. The invention contemplates all such isomers both in pure form and in admixture, including racemic mixtures.

The compounds of formula I can exist in unsolvated as well as solvated forms, including hydrated forms. In general, the solvated forms, with pharmaceutically acceptable solvents such as water, ethanol and the like are equivalent to the unsolvated forms for purposes of the invention.

The compounds which are utilized in the method and composition of this invention are disclosed in U.S. application No. 499,584 filed May 31, 1983, in U.S. application No. 597,887 filed Apr. 9, 1984 and in European published patent application No. 84195923.1 (publication number: 0 127 135). These compounds may be prepared by methods described in those U.S. applications and European published application, the disclosures of which are incorporated herein by reference for that purpose.

The compounds of formula I are useful in the treatment of autoimmune and other immunological diseases including graft rejection in which T cell proliferation is a contributing factor to the pathogenesis of disease. The effectiveness of these compounds as immunosuppressing agents may be demonstrated by the following tests which involve the inhibition of T cell functions using these compounds.

GRAFT VS. HOST REACTION (GVHR)

To induce a GVHR, C57 B1/6XA/J(B6AF1) male mice were injected intravenously with parental (C57B1/6J) spleen and lymph node cells. The compound 10-(4-chlorophenyl)-2,3,4,10-tetrahydro-5H-pyrano[2,3-b][1,8]naphthyridin-5-one (Compound A) was then administered orally for 10 days beginning on the day prior to the cell transfer. On the day following the last treatment, the animals were sacrificed, and their spleens were excised and weighed. The enlargement of the spleen of the host is a result of a GVHR. To some extent it is the host's own cells which infiltrate and enlarge the spleen although they do this because of the presence of graft cells reacting against the host. The amount of spleen enlargement, splenomegaly, is taken as a measure of the severity of the GVHR.

In carrying out the GVHR the animal in the experimental group is injected with parental cells, cells of the same species but of different genotype, which cause a weight increase of the spleen. The animal in the control group is injected with syngeneic cells, genetically identical cells which do not cause a weight increase of the spleen. The effectiveness of Compound A administered to the mice in the experimental group is measured by comparing the spleen weight of the untreated and treated GVH animal with that of the syngeneic control. Compound A reduced spleen weight by 8% as compared to the untreated animals at a dose of 100 mg/kg.

ANTI-SHEEP RED BLOOD CELL RESPONSE

The immunosuppressive activity of the compounds of formula I may also be shown by the inhibition of the secretion of IgM by B. cells in mice immunized with sheep erythrocytes. In particular, BDF$_1$ are mice are immunized intravenously with $1 \times 10^8$ sheep erythrocytes on day zero. Treatment with the test drug (oral administration) is initiated the day prior to the immunization and is continued through day three. On day four the number of IgM secreting cells in the spleens of the treated mice are assessed by the Jerne Plaque technique, with the results expressed as a percent inhibition in comparison to untreated controls. Compound A at 100 mg/kg per day and 9-(3-chlorophenyl)-3,9-dihydro-2-methyl-furo[2,3-b][1,8]naphthyridin-4[2H]-one (Compound B) at 100 mg/kg per day provided about 10% and about 27-36% inhibition, respectively, in this test procedure.

As noted, European patent publication No. 0 127 135 discloses that the subject compounds possess anti-allergy and anti-inflammatory activities. For example, Compound A at a concentration of about 10 μM provided about 57% inhibition of SRS-A release in the procedure described in Kreutner et al., *European Journal of Pharmacology*, Vol. 111, 1985, pp 1-8. Compound A has an $ED_{30}$ value of about 6 mg/kg p.o. in tests measuring the reverse passive Arthus reaction in the pleural cavity of rats (as described by Myers et al., *Inflammation*, Vol. 9, No. 1, 1985, pp. 91-98). These results for Compound A indicate that an immunosuppressive effective dose for the compounds of formula I is several times their anti-inflammatory and anti-allergy effective doses.

The usual dosage range for the compounds of formula I in a 70 kg mammal is a dose of about 0.1 to 250 mg/kg, preferably 0.1 to 150 mg/kg per day. The compounds may be administered by conventional routes, e.g., orally, subcutaneously, intramuscularly, etc. Orally the compound may be administered in 3 or 4 divided doses per day. Of course, the dose will be regulated according to the potency of compound employed, the immunological disease being treated, and the judgment of the attending clinician depending on factors such as the degree and the severity of the disease state and age and general condition of the patient being treated.

To treat immunological diseases, the active compounds of formula I can be administered in unit dosage forms such as tablets, capsules, pills, powders, granules, sterile parenteral solutions or suspensions, suppositories, transdermal compositions and the like. Such dosage forms are prepared according to standard techniques well known in the art.

For preparing pharmaceutical compositions from the compounds described by this invention, inert, pharmaceutically acceptable carriers can be either solid or liquid. Solid form preparations include powders, tablets, dispersible granules, capsules, cachets and suppositories. A solid carrier can be one or more substances which may also act as diluents, flavoring agents, solubilizers, lubricants, suspending agents, binders or tablet disintegrating agents; it can also be an encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets preferably contain from 5 to about 70 percent of the active ingredient. Suitable solid carriers are magnesium carbonate, magnesium strearate, talc, sugar, lactose, pectin, dextrin, starch, gelatin, tragacanth, methylcellulose, sodium carboxymethylcellulose, a low melting wax, cocoa butter and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Liquid form preparations include solutions, suspensions and emulsions. As an example may be mentioned water or water-propylene glycol solutions for parenteral injection. Liquid preparations can also be formulated in solution or suspension in aqueous polyethylene glycol solution. Aqueous solutions suitable for oral use can be prepared by adding the active component in water and adding suitable colorants, flavors, stabilizing, sweetening, solubilizing and thickening agents as desired. Aqueous suspensions suitable for oral use can be made by dispersing the finely divided active component in water with viscous material, i.e., natural or synthetic gums, resins, methylcellulose, sodium carboxymethylcellulose and other well-known suspending agents.

Also included are solid form preparations which are intended to be converted, shortly before use, to liquid form preparations for either oral or parenteral administration. Such liquid forms include solutions, suspensions and emulsions. These particular solid form preparations are most conveniently provided in unit dose form and as such are used to provide a single liquid dosage unit. Alternately, sufficient solid may be provided so that after conversion to liquid form, multiple individual liquid doses may be obtained by measuring predetermined volumes of the liquid form preparation as with a syringe, teaspoon or other volumetric container. When multiple liquid doses are so prepared, it is preferred to maintain the unused portion of said liquid doses at low temperature (i.e., under refrigeration) in order to retard possible decomposition. The solid form preparations intended to be converted to liquid form may contain, in additions to the active material, flavorants, colorants, stabilizers, buffers, artificial and natural sweeteners, dispersants, thickeners, solubilizing agents and the like. The solvent utilized for preparing the liquid form preparation may be water, isotonic water, ethanol, glycerine, propylene glycol and the like as well as mixtures thereof. Naturally, the solvent utilized will be chosen with regard to the route of administration, for example, liquid preparations containing large amounts of ethanol are not suitable for parenteral use.

The composition of the invention may also be deliverable transdermally. The transdermal compositions can take the form of creams, lotions and/or emulsions and can be included in a transdermal patch of the matrix or reservoir type as are conventional in the art for this purpose.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules and powders in vials or ampoules. The unit dosage form can also be appropriate number of any of these in packaged form. The compositions can, if desired, also contain other therapeutic agents.

The dosages may be varied depending upon the requirements of the patient, and severity of the condition being treated and the particular compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The following examples are intended to illustrate, but not to limit, the present invention. The term "Compound A" refers to 10-(4-chlorophenyl)-2,3,4,10-tetrahydro-5H-pyrano[2,3-b][1,8]-naphthyridin-5-one. It is contemplated, however, that this compound may be replaced by equally effective quantities of other compounds of formula I as defined above.

EXAMPLE 1

Tablets

| No. | Ingredient | mg/tablet | mg/tablet |
|---|---|---|---|
| 1 | Compound A | 100 | 500 |
| 2 | Lactose USP | 122 | 113 |
| 3 | Corn Starch, Food Grade, as a 10% paste in Purified Water | 30 | 40 |
| 4 | Corn Starch, Food Grade | 45 | 40 |
| 5 | Magnesium Strearate | 3 | 7 |
|  | Total | 300 | 700 |

Method of Manufacture

Mix Item Nos. 1 and 2 in a suitable mixture for 10–15 minutes. Granulate the mixture with Item No. 3. Mill the damp granules through a coarse screen (e.g., ¼") if needed. Dry the damp granules. Screen the dried granules if needed and mix with the Items No. 4 and mix for 10–15 minutes. Add Item No. 5 and mix for 1–3 minutes. Compress the mixture to appropriate the size and weight on a suitable tablet machine.

EXAMPLE 2

Capsules

| No. | Ingredient | mg/capsule | mg/capsule |
|---|---|---|---|
| 1 | Compound A | 100 | 500 |
| 2 | Lactose USP | 106 | 123 |
| 3 | Corn Starch, Food Grade | 40 | 70 |
| 4 | Magnesium Strearate NF | 4 | 7 |
|  | Total | 250 | 700 |

Method of Manufacture

Mix Item Nos. 1, 2 and 3 in a suitable blender for 10–15 minutes. Add Item No. 4 and mix for 1–3 minutes. Fill the mixture into suitable two-piece hard gelatin capsules on a suitable encapsulating machine.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

We claim:

1. A method of suppressing the T or B cell function of the immune response in a mammal which comprises administering to a mammal in need of such treatment an immunosuppressing effective amount of a compound having the structural formula I:

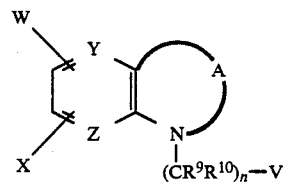

wherein:

A is

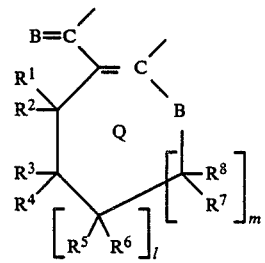

or

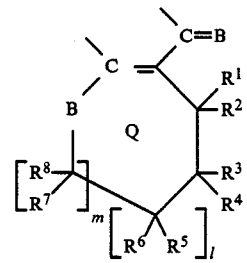

B is independently oxygen or sulfur;

$R^1$–$R^8$ may be the same or different and are hydrogen or alkyl having from 1 to 6 carbon atoms or two adjacent $R^1$–$R^8$ substituents may be combined to form an additional carbon to carbon bond;

l and m may be the same or different and are 0 or one;

the ring labelled, Q, may optionally contain up to two additional double bonds;

n is 0, 1 or 2;

W and X may be the same or different and are hydrogen, hydroxy, alkyl having from 1 to 6 carbon atoms, halogen, nitro, alkoxy having from 1 to 6 cabon atoms, trifluoromethyl, cyano, cycloalkyl having from 3 to 7 carbon atoms, alkenyloxy having from 3 to 6 carbon atoms, alkynyloxy having from 3 to 6 carbon atoms, $S(O)_p$—$R^a$ {wherein p is 0, 1 or 2 and $R^a$ is alkyl having from 1 to 6 carbon atoms}, $NHSO_2R^a$ {wherein $R^a$ is defined herein}, $NHSO_2CF_3$, $NHCOCF_3$, $SO_2NH_2$, $COR^b$ {wherein $R^b$ is OH, $NH_2$ or $OR^a$ (wherein $R^a$ is defined herein)}, O—D—$COR^b$ {wherein D is alkylene having from 1 to 4 carbon atoms and $R^b$ is defined herein}, $NHCOR^c$ {wherein $R^c$ is hydrogen, alkyl having from 1 to 6 carbon atoms, alkoxy having from 1 to 6 carbon atoms, $COR^d$ (wherein $R^d$ is hydroxy or alkoxy having from 1 to 6 carbon atoms) or $NHR^e$ (wherein $R^e$ is hydrogen or alkyl having from 1 to 6 carbon atoms)}, or phenoxy {wherein the benzene ring may be substituted with any of the other substituents W and X};

Y and Z may be the same or different and are CH or N;

V is phenyl, naphthyl, indenyl, indanyl, 2-, 3- or 4-pyridyl, 2-, 3- or 5-pyrimidinyl, 2- or 3-thienyl, 2- or 3-furyl or 2-, 4- or 5-thiazolyl, any of which may be substituted with W and X as defined herein; and $R^9$ and $R^{10}$ are independently hydrogen or alkyl having from 1 to 6 carbon atoms.

2. A method according to claim 1 wherein n in formula I is zero.

3. A method according to claim 2 wherein Y in formula I is CH.

4. A method according to claim 3 wherein said compound has the structural formula:

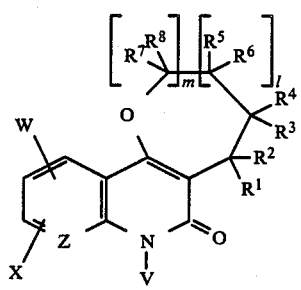
II

5. A method according to claim 4 wherein Z in formula II is N.

6. A method according to claim 5 wherein l and m in formula II are both zero.

7. A method according to claim 5 wherein l and m in formula II are both one.

8. A method according to claim 5 wherein the sum of l and m in formula II is one.

9. A method according to claim 1 wherein B is oxygen.

10. A method according to claim 2 wherein B is oxygen.

11. A method according to claim 3 wherein B is oxygen.

12. A method according to claim 5 wherein V in formula II is

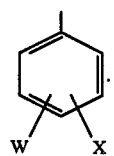

13. A method according to claim 1 wherein said compound has structural formula:

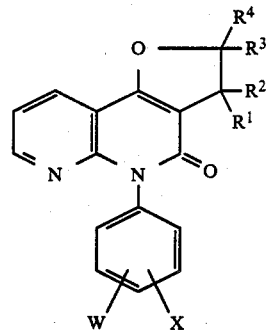
III wherein W, X, V, $R^1$, $R^2$, $R^3$ and $R^4$ are as defined in claim 1.

14. A method according to claim 1 wherein said compound has structural formula:

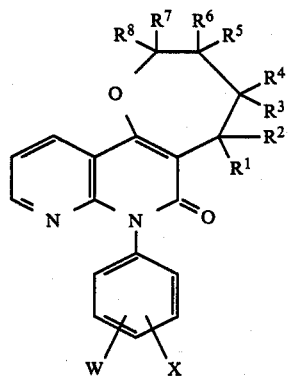
IV wherein W, X, and $R^1$–$R^8$ are as defined in claim 1.

15. A method according to claim 13 wherein $R^1$–$R^4$ are hydrogen or methyl.

16. A method according to claim 14 wherein $R^1$–$R^8$ are hydrogen or methyl.

17. A method according to claim 16 wherein zero or one of $R^1$–$R^8$ is methyl and the rest are hydrogen.

18. A method according to claim 17 wherein W is 3-chloro and X is hydrogen, chlorine or fluorine.

19. A method according to claim 17 wherein W is 3-methoxy and X is hydrogen or fluorine.

20. A method according to claim 17 wherein W and X are both hydrogen.

21. A method according to claim 1 wherein said compound has the structural formula:

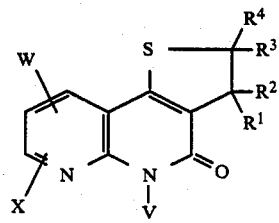

wherein W, X, V, $R^1$, $R^2$, $R^3$ and $R^4$ are as defined in claim 1.

22. A method according to claim 1 wherein said compound has the structural formula:

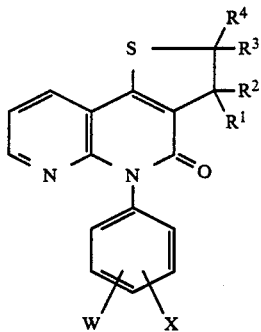

wherein W, X, R¹, R², R³ and R⁴ are as defined in claim 1.

23. A method according to claim 22 wherein W is 3-chloro and X is hydrogen, chlorine or fluorine.

24. A method according to claim 22 wherein W is 3-methoxy and X is hydrogen or fluorine.

25. A method according to claim 22 wherein W and X are both hydrogen.

26. A method according to claim 1 wherein said selected from the group consisting of:
3,5-dihydro-5-phenyl-furo[3,2-c][1,8]naphthyridin4[2H]-one;
3,5-dihydro-5-phenyl-thieno[3,2-c][1,8]-naphthyridin-4[2H]-one;
6-phenyl-2,3,4,6-tetrahydro-pyrano[3,2-c][1,8]naphthyridine-5-one;
2-methyl-3,5-dihydro-5-phenyl-furo[3,2-c][1,8]naphthyridin-4[2H]-one;
3,9-dihydro-9-phenyl-furo[2,3-b][1,8]naphthyridin-4[2H]-one;
3,9-dihydro-9-(p-methylphenyl)-furo[2,3-b][1,8]naphthyridin-4[2H]-one;
3,9-dihydro-2-methyl-9-phenyl-furo[2,3-b][1,8]naphthyridin-4[2H]-one;
3,5-dihydro-5-(p-methylphenyl)-furo[3,2-c][1,8]naphthyridin-4[2H]-one;
3,5-dihydro-5-(p-fluorophenyl)-furo[3,2-c][1,8]naphthyridin-4[2H]-one;
3,5-dihydro-5-(m-methoxyphenyl)-furo[3,2-c][1,8]naphthyridin-4[2H]-one;
3,5-dihydro-5-(m-methylthiophenyl)-furo[3,2-c][1,8]naphthyridin-4[2H]-one;
3,9-dihydro-9-(p-fluorophenyl)-furo[2,3-b][1,8]naphthyridin-4[2H]-one;
3,9-dihydro-9-(m-methoxyphenyl)-furo[2,3-b][1,8]naphthyridin-4[2H]-one;
3,9-dihydro-9-(m-methylthiophenyl)-furo[3,2-c][1,8]naphthyridin-4[2H-one;3,5-dihydro-5-(3,4-dichlorophenyl)-furo[3,2-c][1,8]-naphthyridin-4[2H]-one;
3,5-dihydro-5-(3,4-dichlorophenyl)-2-methyl-furo[3,2-c][1,8]-naphthyridin-4[2H]-one;
3,5-dihydro-5-(4-chlorophenyl)-furo[3,2-c][1,8]naphthyridin-4[2H]-one;
3,5-dihydro-5-(3-chlorophenyl)-furo[3,2-c][1,8]naphthyridin-4[2H]-one;
3,5-dihydro-5-(3-chlorophenyl)-2-methyl-furo[3,2-c][1,8]-naphthyridin-4[2H]-one;
3,5-dihydro-5-(4-fluorophenyl)-2-methyl-furo[3,2-c][1,8]-naphthyridin-4[2H]-one;
3,5-dihydro-5-(3-methoxyphenyl)-2-methyl-furo[3,2-c][1,8]-naphthyridin-4[2H]-one;
3,5-dihydro-5-(3,5-dichlorophenyl)-furo[3,2-c][1,8]naphthyridin-4[2H]-one;
3,5-dihydro-5-(3,5-dichlorophenyl)-2-methyl-furo[3,2-c][1,8]-naphthyridin-4[2H]-one;
3,5-dihydro-5-phenyl-2,2-dimethyl-furo[3,2-c][1,8]naphthyridin-4[2H]-one;
3,5-dihydro-5-(3-methylsulfonylaminophenyl)-2-methylfuro[3,2-c][1,8]-naphthyridin-4[2H]-one;
3,5-dihydro-5-(3-methylsulfonylaminophenyl)-furo[3,2-c][1,8]-naphthyridin-4[2H]-one;
3,9-dihydro-9-(3,4-dichlorophenyl)-furo[2,3-b][1,8]naphthyridin-4[2H]-one;
3,9-dihydro-9-(4-chlorophenyl)-furo[2,3-b][1,8]naphthyridin-4[2H]-one;
3,9-dihydro-9-(3-chlorophenyl)-furo[2,3-b][1,8]naphthyridin-4[2H]-one;
3,9-dihydro-9-(3-chlorophenyl)-2-methyl-furo[2,3-b][1,8]-naphthyridin-4[2H]-one;
3,9-dihydro-9-(4-fluorophenyl)-2-methyl-furo[2,3-b][1,8]-naphthyridin-4[2H]-one;
3,9-dihydro-9-(3-methoxyphenyl)-2-methyl-furo[2,3-b][1,8]-naphthyridin-4[2H]-one;
3,9-dihydro-9-(3,5-dichlorophenyl)-furo[2,3-b][1,8]naphthyridin-4[2H]-one;
3,9-dihydro-9-(3,5-dichlorohenyl)-2-methyl-furo[2,3-b][1,8]-naphthyridin-4[2H]-one;
3,9-dihydro-9-(3-methylsulfonylaminophenyl)-2-methyl-furo[2,3-b][1,8]-naphthyridin-4[2H]-one;
6-(4-chlorophenyl)-2,3,4,6-tetrahydro-5H-pyrano[3,2-c]-[1,8]naphthyridin-5-one;
6-(3,4-dichlorophenyl)-2,3,4,6-tetrahydro-5H-pyrano[3,2-c][1,8]naphthyridin-5-one;
6-(4-methoxyphenyl)-2,3,4,6-tetrahydro-5H-pyrano[3,2-c][1,8]naphthyridin-5-one;
6-(4-methylphenyl)-2,3,4,6-tetrahydro-5H-pyrano[3,2-c][1,8]naphthyridin-5-one;
10-(3,4-dichlorophenyl)-2,3,4,10-tetrahydro-5H-pyrano-[2,3-b][1,8]naphthyridin-5-one;
10-(4-methoxyphenyl)-2,3,4,10-tetrahydro-5H-pyrano[2,3-b][1,8]naphthyridin-5-one;
10-(4-chlorophenyl)-2,3,4,10-tetrahydro-5H-pyrano(2,3-b][1,8]naphthyridin-5-one;
10-(4-methylphenyl)-2,3,4,10-tetrahydro-5H-pyrano(2,3-b][1,8]naphthyridin-5-one;
10-phenyl-2,3,4,10-tetrahydro-5H-pyrano-[2,3-b][1,8]-naphthyridin-5-one;
7-phenyl-3,4,5,7-tetrahydro-oxepino[3,2-c][1,8]naphthyridin-6[2H]-one;
7-(4-chlorophenyl)-3,4,5,7-tetrahydro-oxepino[3,2-c][1,8]-naphthyridin-6[2H]-one;
7-(3-chlorophenyl)-3,4,5,7-tetrahydro-oxepino[3,2-c][1,8]-naphthyridin-6[2H]-one;
7-(3-methoxyphenyl)-3,4,5,7-tetrahydro-oxepino[3,2-c][1,8 -naphthyridin-6[2H]-one; and
7-(3-hydroxyphenyl)-3,4,5,7-tetrahydro-oxepino[3,2-c][1,8]-naphthyridin-6[2H]-one.

27. The method according to claim 1 wherein the compound is administered orally.

28. The method according to claim 26 wherein the compound is administered orally.

* * * * *